United States Patent [19]

Uchiyama et al.

[11] Patent Number: 5,370,798
[45] Date of Patent: Dec. 6, 1994

[54] METHOD FOR CAPTURING METAL IONS

[75] Inventors: Takao Uchiyama, Minoo; Naoshi Imaki, Atsugi; Yuki Takuma, Machida; Masato Aiura, Kawasaki; Eri Hosono, Yokohama, all of Japan

[73] Assignee: Mitsubishi Kasei Corporation, Tokyo, Japan

[21] Appl. No.: 128,274

[22] Filed: Sep. 29, 1993

Related U.S. Application Data

[62] Division of Ser. No. 950,122, Sep. 24, 1992, abandoned.

[30] Foreign Application Priority Data

Sep. 24, 1991 [JP] Japan .................. 3-243819
Aug. 27, 1992 [JP] Japan .................. 4-228839

[51] Int. Cl.$^5$ .............................. B01D 15/00
[52] U.S. Cl. .................. 210/681; 210/682; 210/687; 210/688
[58] Field of Search ............... 210/681, 682, 684, 687, 210/688

[56] References Cited

U.S. PATENT DOCUMENTS 4,908,137 3/1990 Chen et al. .................. 210/688

FOREIGN PATENT DOCUMENTS 2-252701 10/1990 Japan .

OTHER PUBLICATIONS

Hochgesand, A, "Extraction of Metal Picrates by Alkylacyl Cyclodextrin Derivatives", Chemical Abstracts, 116(7):59799; 1990.

*Primary Examiner*—Ivars Cintins
*Attorney, Agent, or Firm*—Oblon, Spivak, McClelland, Maier & Neustadt

[57] ABSTRACT

An agent for capturing metal ions, which consists essentially of a cyclic inulooligosaccharide having from 6 to 8 molecules of fructose bonded by $\beta$-2,1 bonds to form a cyclic structure, wherein hydroxyl groups may all or partially be alkylated.

3 Claims, No Drawings

METHOD FOR CAPTURING METAL IONS

This application is a division of application Ser. No. 07/950,122, filed on Sep. 24, 1992, now abandoned.

BACKGROUND OF THE INVENTION

1. Field of the Invention

The present invention relates to a novel agent for capturing metal ions consisting essentially of a specific cyclic inulooligosaccharide.

2. Discussion of Background

Heretofore, many methods have been proposed for separating and removing metal ions from various compounds or mixtures. As a typical example, there is a method of capturing and recovering metal ions in a solution by means of a chelate compound. Further, a method of recovering metal ions by means of cyclodextrin known to form a clathrate compound, or a method of employing various crown ethers, is also well known.

The method for capturing metal ions by means of a chelate compound had a problem that it was difficult to properly select a chelate compound suitable for the metal ions to be captured, since the capturing performance depends on various factors including the types of the metal ion and the ligand forming the chelate compound and the size of the chelate ring.

In the case of the capturing and recovering method by means of cyclodextrin, cyclodextrin has in its molecule a hydrophobic space by virtue of its specific molecular structure and takes into the space various compounds in an aqueous solution to form a clathrate compound, whereby guest molecules having higher hydrophobic nature tend to be more readily taken into the space. Accordingly, there has been a problem that ions having low hydrophobic nature can not be captured by such cyclodextrin. Further, there has been a problem that cyclodextrin is hardly soluble in water.

The method of employing crown ethers has problems such that crown ethers are insoluble in water, and they are highly toxic to human bodies.

Further, these conventional metal ion capturing agents are all expensive, and their applicable ranges are rather limited.

SUMMARY OF THE INVENTION

The present inventors have previously invented a cyclic inulooligosaccharide having from 6 to 8 molecules of fructose bonded by $\beta$-2,1 bonds to form a cyclic structure (Japanese Unexamined Patent Publication No. 252701/1990). As a result of extensive studies, it has now been found that such a cyclic inulooligosaccharide has a nature of readily bonding to and capturing metal ions, and the present invention has been accomplished on the basis of this discovery.

Thus, the present invention provides an agent for capturing metal ions, which consists essentially of a cyclic inulooligosaccharide having from 6 to 8 molecules of fructose bonded by $\beta$-2,1 bonds to form a cyclic structure, wherein hydroxyl groups may all or partially be alkylated.

DETAILED DESCRIPTION OF THE PREFERRED EMBODIMENTS

Now, the present invention will be described in detail.

The cyclic inulooligosaccharide (hereinafter referred to simply as "the compound of the present invention") having from 6 to 8 molecules of fructose bonded by $\beta$-2,1 bonds to form a cyclic structure, wherein hydroxyl groups may all or partially be alkylated, is a known substance disclosed in Japanese Unexamined Patent Publication No. 2701/1990, or an alkylated product thereof, and it is represented by the following structural formula:

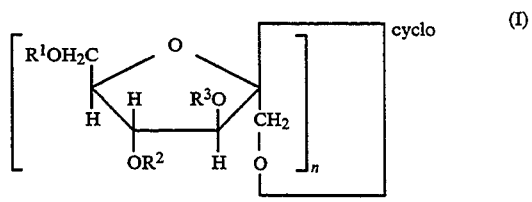

wherein each of $R^1$, $R^2$ and $R^3$ which are independent of each other, is a hydrogen atom or an alkyl group, and n is an integer of 6 to 8.

As disclosed in the above publication or in Japanese Patent Application No. 3983/1991, such a compound can be produced by having acted on inulin an enzyme capable of acting on a $\beta$-2,1 bond fructose polymer having a polymerization degree of at least 8 to form the compound of the present invention by intramolecular rearrangement, or a microorganism capable of producing such an enzyme outside the cells. As such microorganisms and enzymes, Bacillus circulans MZ No. 31 (FRI (Fermentation Research Institute) No. 9943) and Bacillus circulans MCI2554 (FRI No. 11940), and enzymes produced by them, are preferred.

For alkylation of the cyclic inulooligosaccharide, a usual alkylating agent for a hydroxyl group can be employed. For example, an alkyl halide such as methyl iodide, ethyl iodide, propyl iodide, butyl iodide, amyl iodide, octyl iodide, methyl bromide, ethyl bromide, propyl bromide, butyl bromide, amyl bromide, octyl bromide, methyl chloride, ethyl chloride, propyl chloride, butyl chloride, amyl chloride or octyl chloride, is preferably employed, A dialkyl sulfate such as dimethyl sulfate or diethyl sulfate, may also be preferably employed.

Further, a dialkyl carbonate such as dimethyl carbonate, or diethyl carbonate may preferably be employed.

The alkylation may be conducted by reacting the above alkylating agent to the cyclic inulooligosaccharide in the presence or absence of a solvent. If the alkylating agent is present in excess, a compound having all the hydroxyl groups of the polysaccharide alkylated, will be obtained. If the alkylating agent is present in a small amount, a partially alkylated compound will be obtained.

Now, a method for capturing metal ions by means of the compound of the present invention, will be described.

There is no particular restriction as to the metal ions to be captured by the present invention. However, ions of heavy or light metals such as iron (Fe), copper (Cu), zinc (Zn), tin (Sn), antimony (Sb), nickel (Ni), chromium (Cr), manganese (Mn), lead (Pb), cadmium (Cd), silver (Ag), aluminum (Al), lanthanum (La) and cobalt (Co), alkali metals such as lithium (Li), sodium (Na), potassium (K), rubidium (Rb), cesium (Cs) and francium (Fr), and alkaline earth metals such as beryllium (Be), magnesium (Mg), calcium (Ca), strontium (Sr), barium (Ba) and radium (Ra), may be mentioned.

In the present invention, such metal ions to be captured are usually used in the form of the corresponding metal or its salt or other compound and is supplied in the form of a solution such as an aqueous solution or a solution in water and an organic solvent. In such a solution, such metal ions are contacted to the compound of the present invention. As the organic solvent where the metal ions are supplied in the form of a solution in water and an organic solvent, a lower alcohol such as methanol, ethanol, propanol, isopropanol or butanol, or a polar organic solvent such as dimethylformamide, dimethylacetamide, dimethylsulfoxide or N-methylpyrrolidone, is preferred, and such an organic solvent may be mixed with water in an optional proportion.

The metal ion capturing agent of the present invention can be used, for example, for the analysis or separation of metal ions. Specifically, the compound of the present invention is supported on a suitable carrier, and a solution containing the above metal ions is brought in contact therewith. The captured metal ions may be recovered by eluting them with a suitable solvent which is commonly used for chromatographic separation.

Now, the present invention will be described in further detail with reference to Examples. However, it should be understood that the present invention is by no means restricted to such specific Examples.

EXAMPLE 1

A thin layer plate (POLYGRAM IONEX-25 SA-Na, manufactured by Macherey-Nagel Co.; 20 cm×20 cm) was cut into a strip with a width of 2 cm, which was dipped in deionized water until it was completely wet. Then, it was immersed in a 0.1 M aqueous solution of various metal salts and dried in air. Then, cycloinulohexaose (compound of the above formula (I) wherein each of $R^1$, $R^2$ and $R^3$ is hydrogen and n is 6) was spotted and developed. As the developer, water and 50% methanol were employed. After the development for from 1 to 1.5 hours, the strip was dried by a hair dryer, and 5% ethanolic sulfuric acid was sprayed. Then, it was heated at 100° C. for 5 minutes, whereupon the Rf value of a black spot thereby formed, was measured. Further, in accordance with the following formulas for calculation, the clathrate coefficient (k) and the clathrate percentage (% comp.) were obtained. The results are shown in Table 1.

By a thin layer chromatographic principle, the partition coefficient K' is represented by the following formula:

$$K' = xp_m/xp_s\xi \qquad (1)$$

where $xp_m$ and $xp_s$ are molar partition rates of the oligosaccharide p to the mobile phase and to the stationary phase, provided $xp_m + xp_s = 1$, and $\xi$ is the volume ratio of the mobile phase to the stationary phase ($V_m/V_s$). On the other hand, the following formula is generally true:

$$1/K' = \xi(1/Rf - 1) \qquad (2)$$

The clathrate coefficient k is represented by the molar partition ratio of the stationary phase to the mobile phase of the oligosaccharide. Accordingly, from the above formulas (1) and (2), $$k = xp_x/xp_m = 1/Rf - 1$$

The clathrate percentage is represented by the following formula:

% complexed = 100k/(k+1)

Here, Rf' represents the true mobility after eliminating the influence of the interaction between the oligosaccharide and the thin layer carrier, and it is represented by the following formula:

$$Rf' = Rf/Rf_H$$

wherein $Rf_H$ is the mobility when developed by a proton type plate (where no interaction exists between the oligosaccharide and the proton).

Namely, the larger the values for the clathrate coefficient k and the clathrate percentage (% comp.), the larger the capturing effects.

TABLE 1

| Metal ions | Water | | | 50% methanol | | |
|---|---|---|---|---|---|---|
| | Rf | k | % comp. | Rf | k | % comp. |
| $Na^+$ | >0.99 | 0 | 0 | 0.86 | 0.11 | 10.4 |
| $K^+$ | 0.98 | 0.02 | 2.0 | 0.44 | 1.18 | 54.2 |
| $Rb^+$ | 0.96 | 0.04 | 4.0 | 0.40 | 1.40 | 58.3 |
| $Cs^+$ | 0.98 | 0.02 | 2.0 | 0.76 | 0.26 | 20.8 |
| $Cu^{2+}$ | >0.99 | 0 | 0 | 0.88 | 0.09 | 8.3 |
| $Ag^+$ | 0.94 | 0.06 | 6.0 | 0.36–0.74 | 1.66–0.30 | 62.5–22.9 |
| $Ba^{2+}$ | 0.67 | 0.49 | 33.0 | 0.17 | 4.65 | 82.3 |
| $La^{3+}$ | 0.98 | 0.02 | 2.0 | 0.87 | 0.10 | 9.4 |
| $Pb^{2+}$ | 0.95 | 0.05 | 5.0 | 0.23 | 3.17 | 76.0 |
| $Cr^{3+}$ | 0.97 | 0.03 | 3.0 | 0.86 | 0.12 | 10.4 |
| $Fe^{2+}$ | 0.96 | 0.04 | 4.0 | 0.88 | 0.09 | 8.3 |
| $Fe^{3+}$ | 0.99 | 0.01 | 1.0 | 0.88 | 0.09 | 8.3 |
| $Co^{2+}$ | >0.99 | 0 | 0 | 0.87 | 0.10 | 9.4 |

From the above results, it is evident that cycloinulohexaose specifically forms a complex with $Ba^{2+}$ in water and forms a complex with $K^+$, $Rb^+$, $Cs^+$, $Ag^+$ or $Pb^{2+}$ in 50% methanol. Further, it is evident that the capturing effects are higher in the presence of an organic solvent.

EXAMPLE 2

Using cycloinuloheptaose (compound of the above formula (I) wherein each of $R^1$, $R^2$ and $R^3$ is hydrogen and n is 7) instead of cycloinulohexaose, the Rf value was measured, and the clathrate coefficient (k) and the clathrate percentage (% comp.) were obtained in the same manner as in Example 1. The results are shown in Table 2.

TABLE 2

| Metal ions | Water | | | 50% methanol | | |
|---|---|---|---|---|---|---|
| | Rf | k | % comp. | Rf | k | % comp. |
| $Na^+$ | >0.99 | 0 | 0 | 0.90 | 0.04 | 3.8 |
| $K^+$ | >0.99 | 0 | 0 | 0.85 | 0.11 | 9.9 |
| $Rb^+$ | >0.99 | 0 | 0 | 0.86 | 0.09 | 8.3 |
| $Cs^+$ | 0.99 | 0.01 | 1.0 | 0.82 | 0.15 | 13.0 |
| $Cu^{2+}$ | >0.99 | 0 | 0 | 0.92 | 0.02 | 2.0 |
| $Ag^+$ | >0.99 | 0 | 0 | 0.51–0.67 | 0.84–0.40 | 45.6–28.6 |
| $Ba^{2+}$ | 0.99 | 0.01 | 1.0 | 0.89 | 0.06 | 5.7 |
| $Pb^{2+}$ | >0.99 | 0 | 0 | 0.93 | 0.01 | 1.0 |
| $Fe^{2+}$ | >0.99 | 0 | 0 | 0.84 | 0.12 | 10.7 |

EXAMPLE 3

Using cycloinuloocataose (compound of the above formula (I) wherein each of $R^1$, $R^2$ and $R^3$ is hydrogen and n is 8) instead of cycloinulohexaose, the Rf value was measured, and the clathrate coefficient (k) and the clathrate percentage (% comp.) were obtained in the same manner as in Example 1. The results are shown in Table 3.

TABLE 3

| Metal ions | Water | | | 50% methanol | | |
|---|---|---|---|---|---|---|
| | Rf | k | % comp. | Rf | k | % comp. |
| Na⁺ | 0.99 | 0.01 | 1.0 | 0.95 | 0.02 | 2.0 |
| K⁺ | 0.98 | 0.02 | 2.0 | 0.93 | 0.04 | 3.8 |
| Rb⁺ | 0.96 | 0.04 | 3.8 | 0.89 | 0.09 | 8.3 |
| Cs⁺ | 0.95 | 0.05 | 4.8 | 0.89 | 0.09 | 8.3 |
| Cu²⁺ | 0.92 | 0.09 | 8.3 | 0.94 | 0.03 | 2.9 |
| Ag⁺ | 0.98 | 0.02 | 2.0 | 0.89–0.73 | 0.09–0.33 | 8.3–24.8 |
| La³⁺ | 0.98 | 0.02 | 2.0 | 0.89 | 0.09 | 8.3 |
| Pb²⁺ | 0.97 | 0.03 | 2.9 | 0.93 | 0.04 | 3.8 |
| Cr³⁺ | 0.94 | 0.06 | 5.7 | 0.89 | 0.09 | 8.3 |
| Fe²⁺ | 0.98 | 0.02 | 2.0 | 0.88 | 0.10 | 9.1 |
| Fe³⁺ | 0.99 | 0.01 | 1.0 | 0.86 | 0.13 | 11.5 |

EXAMPLE 4

Completely methylated cycloinulohexaose (compound of the above formula (I) wherein each of $R^1$, $R^2$ and $R^3$ is a methyl group and n=6) was added to a 0.1 M solution of various metal salts in deuterated methanol ($CD_3OD$)/heavy water ($D_2O$)=7/3 (volume ratio), in a molar ratio of from 1/10 to 1/20 relative to the metal salts. After being left to stand at room temperature for about 1 hour, this solution was measured by NMR manufactured by Barian [UNITY-300 (300 MHz)], and the induced shift of proton ($\Delta\delta$(ppm)) was observed as compared with the case where no metal salt was present.

According to the NMR principle, the larger the induced shift, the larger the capturing effects.

The results are shown in Table 4.

TABLE 4

| Metal salts | Difference in the induced shift ($\Delta\delta$ (ppm)) | | | | | | |
|---|---|---|---|---|---|---|---|
| [Proton species] | 1A | 1B | 3 | 4 | 5 | 6A | 6B |
| 1. NaCl | −0.02 | 0.02 | 0 | 0.02 | 0.01 | — | — |
| 2. KCl | — | — | 0.02 | 0.13 | — | — | — |
| 3. CsCl | −0.08 | 0.13 | — | — | — | — | — |
| 4. BaCl₂.H₂O | — | 0.01 | — | — | 0 | — | — |

TABLE 4-continued

| Metal salts | Difference in the induced shift ($\Delta\delta$ (ppm)) | | | | | | |
|---|---|---|---|---|---|---|---|
| [Proton species] | 1A | 1B | 3 | 4 | 5 | 6A | 6B |
| 5. Pb(NO₃)₂ | 0 | 0.01 | 0 | 0.01 | 0.01 | — | — |

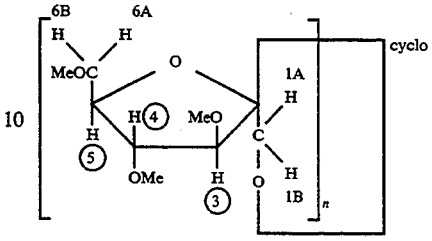

From the above results, it is apparent that the completely methylated cycloinulohexaose specifically forms a complex with K⁺ or Cs⁺.

As described in the foregoing, it is possible to easily capture metal ions by means of the capturing agent of the present invention. Thus, the capturing agent of the present invention is useful for the analysis or separation of metal ions.

What is claimed is:

1. A method for capturing metal ions, which comprises capturing metal ions in solution in an organic solvent by contacting said solution with a metal ion capturing agent consisting essentially of a cyclic inulooligosaccharide having from 6 to 8 molecules of fructose bonded by β-2,1 bonds to form a cyclic structure, wherein said cyclic structure contains hydroxyl groups, alkoxy groups or a combination of hydroxyl and alkoxy groups.

2. The method according to claim 1, wherein the cyclic inulooligosaccharide contains methoxy groups.

3. The method according to claim 1, wherein the cyclic inulooligosaccharide is of the formula

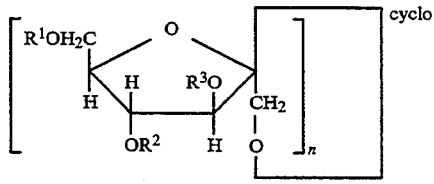

wherein each of $R^1$, $R^2$ and $R^3$ which are independent of each other, is a hydrogen atom or an alkyl group, and n is an integer of 6 to 8.

* * * * *